| United States Patent [19] | [11] Patent Number: 4,911,953 |
| Hosonuma et al. | [45] Date of Patent: Mar. 27, 1990 |

[54] PROCESS FOR PRODUCING COMPOSITE MATERIALS HAVING A COATING OF CALCIUM PHOSPHATE COMPOUND

[75] Inventors: Masashi Hosonuma, Kanagawa; Takayuki Shimamune, Tokyo, both of Japan

[73] Assignee: Permelec Electrode Ltd., Kanagawa, Japan

[21] Appl. No.: 267,974

[22] Filed: Sep. 29, 1988

[30] Foreign Application Priority Data

Sep. 29, 1987 [JP] Japan ................... 62-245576

[51] Int. Cl.$^4$ .......................... B05D 3/08; B05D 3/02
[52] U.S. Cl. ........................ 427/224; 427/2; 427/226; 427/343; 427/377
[58] Field of Search ............... 427/226, 224, 377, 343, 427/2

[56] References Cited

U.S. PATENT DOCUMENTS

| 3,709,723 | 1/1973 | Watanabe et al. | 427/226 |
| 4,687,675 | 8/1987 | Nakano et al. | 427/2 |
| 4,705,694 | 11/1987 | Buttazzoni et al. | 427/2 |
| 4,794,023 | 12/1988 | Shimamune et al. | 427/350 |
| 4,818,572 | 4/1989 | Shimamune et al. | 427/327 |

*Primary Examiner*—Janyce Bell
*Attorney, Agent, or Firm*—Sughrue, Mion, Zinn, Macpeak & Seas

[57] ABSTRACT

A process for producing a composite material having a coating of a calcium phosphate compound on the surface of a metal substrate, said process comprising the steps of applying a coating solution of an organic calcium compound and an organophosphorus compound in an organic solvent to the surface of said metal substrate, and firing the applied solution to form a coated layer of a calcium phosphate compound on the surface of said metal substrate.

11 Claims, No Drawings

PROCESS FOR PRODUCING COMPOSITE MATERIALS HAVING A COATING OF CALCIUM PHOSPHATE COMPOUND

FIELD OF THE INVENTION

The present invention relates to a process for producing a composite material comprising a metal substrate such as titanium, a titanium alloy or a stainless steel alloy the surface of which is coated with a calcium phosphate compound having particularly good compatibility with bone or tooth tissues. The composite material produced by this method is useful not only as an implant such as artificial bones, teeth and tooth roots but also as a joining material therefor.

BACKGROUND OF THE INVENTION

Biological implants such as artificial bones or tooth roots have recently attracted attention because when bones or teeth are broken or otherwise damaged or destroyed by an accident, etc., the implants can be bonded to the remaining bone or implanted, e.g., in the case of tooth roots, in the bones of the jaw, and thus can be used in a form close to natural bones or teeth and ensure maintenance of comfortable daily lives. Since these implants are to be embedded in the body, they should be nontoxic to the body. They also must have various other properties, such as sufficient strength, good moldability or workability, freedom from dissolution, moderate specific gravity, and biocompatibility.

Alpha-alumina, noble metals and alloys such as stainless steel have been used as implants but they fail to satisfy one or more of the requirements set forth above. Furthermore, they have a common problem in that they are not biocompatibile.

Recently, apatite ceramics have been proposed as materials that are claimed to satisfy all of the requirements that should be met by ideal implants. Apatite ceramics are chiefly composed of calcium phosphate compounds. Since the main components of bones and teeth are also calcium phosphate compounds, apatite ceramics exhibit very good biocompatibility and can be readily assimilated by living tissues after they are implanted in the body. However, apatite ceramics still suffer the problems of low strength and low workability and their use has been limited.

In order to eliminate these problems, techniques are required that are capable of joining ceramics to either metals or ceramics to produce strong adhesion. Plasma spraying and sputtering are two known techniques suitable for this purpose. While the plasma spray method is useful in achieving the joints described above, it has various defects: for example, difficulty in applying uniform coatings on the entire surface of a complexly shaped material exists; all surfaces of a porous material cannot be coated; an expensive apparatus is required; the efficiency of utilization of expensive apatite particles is low; and strong adhesion between the coating and the substrate is not always provided. A sputtering process also has several defects, such as high cost and the inability to produce coatings thicker than 1 $\mu$m and, therefore, the thickness of coatings cannot be appropriately adjusted in accordance with the specific use.

With a view to eliminating the defects of apatite ceramics, the present inventors previously proposed a process for forming a layer of calcium phosphate compound on a substrate by firing a coating made from a nitric or hydrochloric acid aqueous solution of a calcium phosphate compound, as well as a composite material produced by this process (see Japanese Patent Application No. 64012/86). The proposed method has the advantage that a uniform coating layer can be formed on the surface of a substrate of any shape. However, in this method, the calcium phosphate compound is directly precipitated from its aqueous solution and deposited on the surface of the substrate, so the adhesion between the substrate and the deposited coating of calcium phosphate compound is rather weak and prone to failure (i.e., delamination) on extended use.

As will be described immediately below, a principal object of the present invention is to attain strong adhesion between a substrate and a calcium phosphate compound by employing an organic compound. The use of an organic compound in the production of hydroxyapatite is known and in the process described in JP-A-61-295215 (the term "JP-A" as used herein refers to a "published unexamined Japanese patent application"), hydroxyapatite is produced through the reaction between a calcium alkoxide and phosphoric acid. But this method is directed to the production f a hydroxyapatite powder itself and is not intended for improving the adhesion between a coating of this hydroxyapatite and a substrate.

SUMMARY OF THE INVENTION

An object, therefore, of the present invention is to provide a process for producing a durable composite implant material that has a surface coating of calcium phosphate compound and which is free from the problem of low adhesion between the surface coating and the substrate, thereby assuring the capability of prolonged use without delamination of the coating of calcium phosphate compound.

This object of the present invention is attained by a process comprising forming a coating layer of a calcium phosphate compound on the surface of a metal substrate by first applying a coating solution of an organic calcium compound and an organophosphorus compound in an organic solvent onto the surface of the substrate, and then firing the applied coating layer.

DETAILED DESCRIPTION OF THE INVENTION

The present invention provides a process for producing a composite material having a coating of a calcium phosphate compound, in which a solution containing an organic calcium compound and an organophosphorus compound, and optionally water, in an organic solvent is applied to a metal substrate such as titanium, a titanium alloy or a stainless steel alloy, and the substrate is then fired to form a surface coating layer of calcium phosphate compounds, typically hydroxyapatite and tricalcium phosphate. This process of the present invention is capable of providing a composite material with strong adhesion between the surface coating layer and the metal substrate.

The term "calcium phosphate compound" as used herein generally refers to hydroxyapatite but it also covers tricalcium phosphate, calcium hydrogenphosphate and calcium dihydrogenphosphate which are believed to be formed as by-products of the firing of hydroxyapatite in the process of the present invention, as well as other calcium phosphate based compounds that are formed by reaction between impurity components or substrate components and hydroxyapatite or tricalcium phosphate.

The metal of the meal substrate for use in the present invention is selected from among those which are stable in the body, such as titanium, titanium alloys, and stainless steel alloys. Titanium and titanium alloys can be metallic titanium and titanium alloys with alloying elements, such as Ta, Nb, platinum group metals, Al and V. Suitable stainless steel alloys are not only conventional stainless steels such as JIS SUS 304, 310 and 316 but also corrosion resistant alloys such as cobalt-chromium alloys that are suitable for implantation in the body. The metal substrates made of the above-described metals or alloys may assume any shape, such as a plate, a rod or other smooth-surfaced bodies, a sponge having a porous surface, as well as an expanded mesh and a porous plate. These substrates are employed since they have satisfactorily high mechanical strength and are easy to work as compared with sintered bodies and glass. If desired, the substrates may be cleaned with water, acids, ultrasonic waves, vapor or otherwise cleaned to improve the affinity of their surfaces for the calcium phosphate compounds and other compounds to be deposited on the substrates. It is also possible to roughen the surfaces of the substrates by blasting and/or etching not only to improve their affinity for the calcium phosphate compounds and other compounds to be deposited on the substrates but also to activate their surfaces. Etching of the substrate surfaces may be accomplished not only by chemical methods but also by physical methods including sputtering.

After preparing the substrate in the manner described above, a solution containing an organic calcium compound and an organophosphorus compound, and optionally water, in an organic solvent is applied to the surface of the substrate and fired with heat to form a coating layer of a calcium phosphate compound that adheres strongly to the metal substrate.

Examples of organic calcium compounds that can be used in the present invention are metal soaps that are chemically stable and which are soluble in organic solvents, as illustrated by calcium salts of carboxylic acids such as naphthenic acid, 2-ethylhexanoic acid, stearic acid, tall oil aliphatic acids and soybean oil aliphatic acids. In particular, a calcium salt of 2-ethylhexanoic acid is advantageously used since it has a fixed chemical composition and is capable of containing a greater amount of calcium by virtue of its comparatively low molecular weight. Theoretically, 2-ethylhexanoic acid is capable of containing up to about 12% by weight calcium but in order to remove the carbon dioxide dissolved in the coating solution, it is preferable for some of the 2-ethylhexanoic acid to remain unreacted, thereby preparing calcium 2-ethylhexanoate solution containing 5 to 7% by weight calcium. While the above-mentioned metal soaps are preferably used as organic calcium compounds, other organic compounds such as calcium alcoholates may also be employed.

Commercially available metal soaps may be used per se as organic calcium compounds. Alternatively, organic calcium compounds to be used in the present invention may be prepared by reaction between a corresponding carboxylic acid and an inorganic calcium compound such as calcium oxide.

Illustrative organophosphorus compounds that can be used in the present invention are phosphate esters that are chemically stable and which are soluble in organic solvents, such as trimethyl phosphate, tri-n-butyl phosphate, tricresyl phosphate, tri(2-ethylhexyl) phosphate, di-n-butyl phosphate and di(2-ethylhexyl) phosphate. In order to remove the carbon dioxide dissolved in the coating solution, it is preferable for the organophosphorus compound to be rendered acidic by making part or all of it comprise a di- or monoester of phosphoric acid such as di(2-ethylhexyl) phosphate.

The solvent used in the present invention must have the ability to form a stable solution of the organic calcium compound and the organophosphorus compound. Preferably, the solvent is miscible with water and is capable of providing various concentrations of the solutes. Therefore, an organic solvent is employed in the present invention. Advantageous organic solvents include ethyl alcohol, isopropyl alcohol, n-butyl alcohol, ethylene glycol, ethylene glycol monoethyl ether, glycerin and mixtures thereof. Besides these alcohols, other organic solvents may be employed.

The organic solvent having the organic calcium compound and the organophosphorus compound dissolved therein may or may not contain water. The addition of water and the composition of the coating solution depend on the type of the calcium phosphate compound to be deposited as a coating layer on the substrate. If hydroxyapatite is to be formed as a coating of calcium phosphate compound, the molar ratio of calcium to phosphorus is adjusted to 5:3 so as to attain the chemical composition of hydroxyapatite, $Ca_{10}(PO_4)_6(OH)_2$. In addition, water is incorporated as a source of hydroxyl groups in this chemical composition. Since water will readily evaporate during the coating operation, it is added in a more-than-stoichiometric amount that provides a $Ca/H_2O$ molar ratio of 2.5. Ig tricalcium phosphate is to be deposited as a coating of calcium phosphate compound, the molar ratio of calcium to phosphorus is adjusted to 3:2 so as to attain the chemical composition of tricalcium phosphate, $Ca_3(PO_4)_2$. Water need not be added to produce tricalcium phosphate. As described above, the addition of water is optional in the process of the present invention but water is preferably added since this results in the formation of highly crystalline hydroxyapatite.

The coating solution may be applied to the surface of the metal substrate by any of the known methods including spin coating, spray coating, dip coating, brush coating and electrostatic coating. If desired, the coating solution may be applied by a printing method after a thickening agent such as acetyl cellulose or ethyl cellulose is incorporated in it.

The metal substrate to which the coating solution has been applied is then fired to produce a desired composite material having a surface coating of calcium phosphate compound on the metal substrate. The firing temperature is preferably in the range of from 300° to 900° C. Below 300° C., the calcium phosphate compound will not fully crystallize. Above 900° C., the surface of the metal substrate will be rapidly oxidized to prevent strong adhesion of the calcium phosphate compound to the substrate. If the heating of the substrate is performed in a non-oxidizing atmosphere, the organic calcium compound and the organophosphorus compound will be decomposed insufficiently to avoid the occurrence of residual carbon. Therefore, the substrate is preferably heated in an oxidizing atmosphere such as oxygen, ozone, water vapor or air. Even in an oxidizing atmosphere, a certain amount of carbon may remain to cause slight darkening of the layer of calcium phosphate compound but a desired white layer can be obtained by burning with a flame. If no acidic components are present in the coating solution, calcium oxide, calcium hydroxide or calcium carbonate might form at a temperature of about 600° C. or below but by heating the substrate above 600° C., the yield of the desired calcium phosphate compound is increased and the production of calcium oxide, calcium hydroxide and calcium carbonate is gradually decreased. Since calcium carbonate will remain even at temperatures higher than 900° C., it is desirable for carbon dioxide to be removed from water employed in the coating solution. It is also desirable that the coating and firing operations are performed in a carbon dioxide free atmosphere. Removal of carbon dioxide may be accomplished by passing water through an aqueous alkaline solution such as an aqueous solution of sodium hydroxide. The formation of calcium carbonate may be conveniently prevented by adding water to the coating solution after it has been rendered slightly acidic with a suitable acid such as nitric acid.

The coating layer formed by the method described above is composed of a calcium compound having a satisfactorily high crystallinity. However, in order to achieve high process efficiency, it is sometimes necessary to effect rapid temperature elevation in the firing step and in such a case, only a calcium phosphate compound having a somewhat low degree of crystallinity will result. If no water is present in the coating solution, the coating layer obtained is not composed of hydroxyapatite crystals but instead they are decomposed into tricalcium phosphate, calcium oxide, etc. In these cases, a hydrothermal treatment may be performed in order to increase the crystallinity of the calcium phosphate compound to be obtained. A hydrothermal treatment denotes a method of crystal growth that is carried out in the presence of water at high temperatures, especially in the presence of water at high temperatures and pressures. The conditions for this hydrothermal treatment are not particularly limited but desirably it is carried out in an autoclave at a temperature of 100° to 200° C. under a pressure of about 1 to 16 kg/cm$^2$ in the presence of steam. This results in an increase in the crystallinity of the coating layer.

By the method described above, a coating layer of a calcium phosphate compound which is chiefly hydroxyapatite or tricalcium phosphate can be formed on the surface of a metal substrate. If a desired thickness of the coating layer is not attained by a single run, the coating and firing operations may be repeated until the desired thickness is attained.

The coating solution employed in the present invention is based on an organic solvent and will not dissolve either hydroxyapatite or tricalcium phosphate. Therefore, the coating and firing operations can be repeated to ensure the formation of coating layer in superposition without dissolution of underlying layers occurring. In addition, no precipitate at ordinary temperatures will form in the coating solution, so the solution will remain stable for a prolonged period and ensures consistent results even if it is used after extended storage.

In the process of the present invention, a coating solution is applied to a substrate, which is then heated to crystallize a calcium phosphate compound from the applied coating solution. This method offers the advantage that a uniform coating layer can be formed over the entire surface of a substrate of any shape.

The following examples are provided for the purpose of further illustrating the present invention but are in no way to be taken as limiting. Unless otherwise indicated, all percents are by weight.

EXAMPLE 1

Calcium carbonate was heated at 1,050° C. for 2 hours at a reduced pressure of $1 \times 10^{-3}$ to $1 \times 10^{-4}$ mmHg to effect conversion to calcium oxide. A portion (1.22 g) of the resulting calcium oxide and 9.93 g of 2-ethylhexanoic acid were charged into a flask equipped with a reflux condenser and dissolved by heating at about 120° C. After cooling the contents of the flask, 16.0 g of n-butyl alcohol, 3.87 g of di(2-ethylhexyl) phosphate and 2.52 g of distilled water were added and the mixture was stirred well to form a coating solution. The proportions of calcium, phosphorus and water in the coating solution were adjusted to be Ca:P:H$_2$O=5:3:40 in molar ratio.

The surface of a titanium plate (JIS, Type 1) having a thickness of 1 mm was grained by blasting with a corundum grit of size #70 and then etched by immersion in a 25% HCl aqueous solution at 60° C. for 24 hours.

The previously prepared coating solution was applied to one side of the titanium plate, which was heated to 600° C. in the air at a rate of 10° C./min and held at that temperature for 10 minutes. After cooling with air, the substrate was roasted with the flame of city gas for 20 to 30 seconds to burn away the residual carbon content.

By repeating the cycle of coating and firing operations four more times, a white surface layer formed on the titanium substrate. The crystalline phase of this coating layer was analyzed by X-ray diffraction. Besides the diffraction peak for titanium in the substrate, the resulting diffraction scan showed only a characteristic peak of hydroxyapatite, indicating that the coating layer was formed of highly crystalline hydroxyapatite.

EXAMPLE 2

Calcium carbonate was heated at 1,050° C. for 2 hours at a reduced pressure of $1 \times 10^{-3}$ to $1 \times 10^{-4}$ mmHg to effect conversion to calcium oxide. A portion (1.22 g) of the resulting calcium oxide and 15.26 g of 2-ethylhexanoic acid were charged into a flask equipped with a reflux condenser and dissolved by heating at about 120° C. After cooling the contents of the flask, 16.0 g of n-butyl alcohol, 3.20 g of tri-n-butyl phosphate and 2.53 g of distilled water were added and the mixture was stirred well to form a coating solution. The proportions of calcium, phosphorus and water in the coating solution were adjusted to be Ca:P:H$_2$O=5:3:40 in molar ratio.

The surface of a titanium plate (JIS, Type 1) having a thickness of 1 mm was grained by blasting with a corundum grit of size #70 and then etched by immersion in a 25% HCl aqueous solution at 60° C. for 24 hours.

The previously prepared coating solution was applied to one side of the titanium plate, which was heated to 600° C. in the air at a rate of 10° C./min and held at that temperature for 10 minutes. After cooling with air, the substrate was roasted with the flame of city gas for 20 to 30 seconds to burn away the residual carbon content.

By repeating the cycle of coating and firing operations four more times, a white surface layer formed on the titanium substrate. The crystalline phase of this coating layer was analyzed by X-ray diffraction. Besides the diffraction peak for titanium in the substrate, the resulting diffraction scan showed a peak for a mixture of hydroxyapatite, hydrated tricalcium phosphate and calcium hydroxide. The substrate was further heated at 850° C. in the air atmosphere, held at that temperature for 30 minutes and cooled thereafter. Analysis by X-ray diffraction showed only a characteristic peak of hydroxyapatite in addition to the peak for titanium in the substrate. This indicates that the coating layer was formed of highly crystalline hydroxyapatite.

EXAMPLE 3

Calcium carbonate was heated at 1,050° C. for 2 hours at a reduced pressure of $1 \times 10^{-3}$ to $1 \times 10^{-4}$ mmHg to effect conversion to calcium oxide. A portion (1.22 g) of the resulting calcium oxide and 15.26 g of naphthenic acid were charged into a flask equipped with a reflux condenser and dissolved by heating at about 150° C. As a result, calcium naphthenate containing 5% calcium was formed. Upon cooling, this product turned into a hard syrupy material. To this material, 16.0 g of n-butyl alcohol, 4.42 g of tricresyl phosphate and 2.55 g of a 1% aqueous nitric acid solution were added and the mixture was stirred well to form a coating solution. The proportions of calcium, phosphorus and water in the coating solution were adjusted to be $Ca:P:H_2O = 5.3:40$ in molar ratio.

A cylindrical 99.5% alumina vessel (i.d., 5 mm) was closely packed with a Co-Cr-Mo alloy rod (dia. 3 mm, equivalent to ASTM F75) and the spherical particles (25 to 40 mesh) of Co-Cr-Mo alloy (equivalent to ASTM F75) prepared by the rotating electrode process, and sintering was performed at 1,200° C. for 3 hours at a reduced pressure of $1 \times 10^{-4}$ to $1 \times 10^{-5}$ mmHg so as to produce a Co-Cr-Mo alloy rod having a porous surface. In order to activate its surface, this rod was immersed in a 5% aqueous HC solution at 60° C. for 20 minutes and cleaned with ultrasonic waves in pure water. Thereafter, the rod was dried.

The cobalt alloy rod was submerged in the previously prepared coating solution, rapidly spun at a rotational speed of 1,000 rpm and centrifuged to remove excess coating solution. Thereafter, the rod was transferred into an air stream, heated to 600° C. at a rate of 10° C./min and held at that temperature for 10 minutes. After cooling with air, the rod was roasted with the flame of city gas for 20 to 30 seconds to burn away the residual carbon content.

By repeating the cycle of coating and firing operations four more times, a white surface layer formed on the Co alloy rod and this layer was found to consist of satisfactory crystalline hydroxyapatite by X-ray diffraction analysis. Examination of a cross section of the sample under a scanning electron microscope showed that the coating layer of hydroxyapatite covered the surface of the Co alloy rod without completely closing the interstices between the Co alloy spheres.

In the process of the present invention for forming a coating layer of calcium phosphate compound on the surface of a metal substrate such as a titanium plate, a calcium phosphate compound of interest is not directly coated on the substrate; instead, an organic calcium compound and an organophosphorus compound are used as sources of calcium and phosphorus for said calcium phosphate compound and a coating solution of these organic compounds in an organic solvent is applied to the surface of the metal substrate and fired to form a desired coating layer of calcium phosphate compound. The present invention therefore offers the following advantages.

Firstly, when the organic calcium compound and organophosphorus compound applied to the substrate are fired, they react on the surface of the substrate to form a calcium phosphate compound in which they strongly adhere to each other to produce a durable coating layer. Since this coating layer binds strongly to the substrate, the composite material produced by the process of the present invention in which the metal substrate is covered with a coating layer of calcium phosphate compound can be stored or used for a prolonged period without experiencing any trouble such as delamination of the surface layer.

Secondly, a coating layer of calcium phosphate compound having the necessary thickness can rarely be formed by a single cycle of coating and firing operations and often multiple coatings must be applied to produce a layer of the desired thickness. In the prior art, water is used as the solvent for the coating solution and part of the first applied coating will dissolve out during subsequent coating operations, thereby making it difficult to produce a fully uniform and durable coating layer. However, in the process of the present invention which employs an organic solvent, the layer first applied to form an undercoat will not dissolve out and a uniform and durable coating layer can be formed by application of multiple coatings.

Thirdly, the composite material produced by the process of the present invention employs titanium, a titanium alloy or a stainless steel alloy as the substrate, so it is nontoxic to the human body and remains stable without dissolving out even when it is worked into an artificial bone or tooth root. Furthermore, the composite material is light in weight and has sufficiently high mechanical strength. It is also easy to work.

Fourthly, the composite material produced by the present invention has a coating of calcium phosphate compound formed on the surface of the substrate, so it has sufficiently good biocompatibility and can be joined easily to body tissues without sacrificing the strength of adhesion.

Fifthly, in the process of the present invention, a desired calcium phosphate compound precipitates from a coating solution through a thermal decomposition reaction, so a uniform coating of this calcium phosphate compound can be formed over the entire surface of a substrate of any shape.

While the invention has been described in detail and with reference to specific embodiments thereof, it will be apparent to one skilled in the art that various changes and modifications can be made therein without departing from the spirit and scope thereof.

What is claimed is:

1. A process for producing a composite material having a coating of a calcium phosphate compound on the surface of a metal substrate, said process comprising the steps of
    applying a coating solution of an organic calcium compound and an organophosphorus compound dissolved in an water miscible organic solvent to the surface of said metal substrate, and
    firing the applied solution to form a coated layer of a calcium phosphate compound on the surface of said metal substrate.

2. A process according to claim 1, wherein said metal substrate is made of a metal or an alloy selected from the group consisting of titanium, titanium alloys, stainless steel and a cobalt-chromium alloy.

3. A process according to claim 1, wherein said coating solution contains water or a dilute aqueous solution of nitric acid so that hydroxyapatite will be chiefly produced as the calcium phosphate compound.

4. A process according to claim 1, wherein said organic calcium compound is calcium 2-ethylhexanoate.

5. A process according to claim 1, wherein said organophosphorus compound is di(2-ethylhexyl) phosphate.

6. A process according to claim 1, wherein said organic solvent is n-butyl alcohol.

7. A process according to claim 1, wherein said process additionally includes removing carbon dioxide from the system either before, during the firing step or both before and during the firing step.

8. A process according to claim 1, wherein the firing is at a temperature between 300° and 900° C.

9. A process according to claim 1, wherein the firing is performed in an oxidizing atmosphere.

10. A process according to claim 1, wherein the process additionally includes removing any remaining carbon after the firing by burning with a flame.

11. A process according to claim 1, wherein the process additionally includes hydrothermally treating the substrate having the coating layer of a calcium phosphate compound formed on its surface by the firing step at 100° to 200° C. in steam so as to modify said coating layer.

* * * * *